(12) United States Patent
Chow et al.

(10) Patent No.: US 11,202,921 B2
(45) Date of Patent: Dec. 21, 2021

(54) INFANT PHOTOTHERAPY DEVICE, METHOD OF USE, AND KIT THEREFOR

(71) Applicant: AVALON PHOTONICS (HK) LIMITED, Sha Tin (HK)

(72) Inventors: Sai Keung Chow, Ma On Shan (HK); Chun Lung Choi, Tsing Yi (HK); Chi Yeung Mang, Tsing Yi (HK); Chun Ho Wong, Fo Tan (HK); Johnson Yiu-Nam Lau, Houston, TX (US)

(73) Assignee: AVALON PHOTONICS (HK) LIMITED, Sha Tin (HK)

( * ) Notice: Subject to any disclaimer, the term of this patent is extended or adjusted under 35 U.S.C. 154(b) by 0 days.

(21) Appl. No.: 16/718,525

(22) Filed: Dec. 18, 2019

(65) Prior Publication Data

US 2020/0197721 A1 Jun. 25, 2020

(30) Foreign Application Priority Data

Dec. 19, 2018 (HK) .................................. 18116291.2

(51) Int. Cl.
*A61N 5/06* (2006.01)
(52) U.S. Cl.
CPC ...... *A61N 5/0621* (2013.01); *A61N 2005/063* (2013.01); *A61N 2005/0632* (2013.01); *A61N 2005/0636* (2013.01); *A61N 2005/0663* (2013.01); *A61N 2005/0664* (2013.01)
(58) Field of Classification Search
CPC ...... A61N 2005/0636; A61N 2005/063; A61N 2005/0645; A61N 2005/0632; A61N 2005/0642; A61N 5/0621
See application file for complete search history.

(56) References Cited

U.S. PATENT DOCUMENTS

| 4,907,132 A | 3/1990 | Parker |
| 6,464,715 B1 | 10/2002 | Gysens et al. |
| 6,494,899 B1 * | 12/2002 | Griffin ................. A61N 5/0621 |
| | | 607/88 |

(Continued)

FOREIGN PATENT DOCUMENTS

WO WO-2017038655 A1 * 3/2017 ............... A61N 5/06

OTHER PUBLICATIONS

Extended European Search Report dated Apr. 17, 2020 in related European Application No. 19216586.8 filed Dec. 18, 2019 (7 pages).

(Continued)

*Primary Examiner* — Carl H Layno
*Assistant Examiner* — Aya Ziad Bakkar
(74) *Attorney, Agent, or Firm* — Daniel F. Nesbitt; Hasse & Nesbitt LLC

(57) ABSTRACT

A phototherapy device, a kit containing such a phototherapy device, and a method for treating a patient with a phototherapy device, the phototherapy device containing a housing, an emission portion, and a light tube, the housing containing a light source that emits light at a wavelength of from about 400 nm to about 550 nm, and may contain a light shield proximal to the light source, the emission portion being distal form the housing and connected thereto via a light tube which contains an optical fibre, and a mesh that may enclose the optical fibre and may allow a limited amount of light to leak from the optical fibre to the outside environment.

20 Claims, 4 Drawing Sheets

(56) References Cited

U.S. PATENT DOCUMENTS

| | | |
|---|---|---|
| 6,596,016 B1 | 7/2003 | Vreman et al. |
| 7,246,392 B2 | 7/2007 | Schmid et al. |
| 2002/0029071 A1 | 3/2002 | Whitehurst |
| 2006/0100675 A1 | 5/2006 | Gardner |
| 2007/0208397 A1 | 9/2007 | Gardner |
| 2009/0030490 A1* | 1/2009 | Pipe .................. A61N 5/0621 607/91 |
| 2010/0106228 A1 | 4/2010 | Gardner |
| 2010/0114263 A1* | 5/2010 | Pressler ............. A61N 5/0621 607/88 |
| 2018/0207446 A1 | 7/2018 | Jones |

OTHER PUBLICATIONS

"GE BiliSoft Phototherapy for Jaundice Review| Ft. Labor & Delivery Nurses | GE Healthcare", Youtube, https://www.youtube.com/watch?v=7uVwlS2qzbQ, Oct. 11, 2018, 1 page.

"BiliSoft™ LED Phototherapy System" Service Manual, M1110150, Rev. 2, www.gehealthcare.com, 2007 Datex-Ohmeda, 44 pages.

"BiliSoft 2.0 Phototherapy System", Intensive therapy, as easy as wrapping a baby in a blanket, www.gehealthcare.com, 2018, 8 pages.

Chapter 6: Spare Parts, 2007, General Electric Company, M1110150 006, 6 pages.

"BiliSoft LED Phototherapy System", Intensive Therapy, as easy as wrapping a baby in a blanket, www.gehealthcare.com, 2007, 8 pages.

\* cited by examiner

ID OF THE INVENTION

The present invention relates to a phototherapy device, method and kit. More specifically, the present invention relates to a phototherapy device, method and kit for treating a patient, typically an infant.

BACKGROUND OF THE INVENTION

Devices, methods and kits are known to provide phototherapy treatments to patients such as children and infants, especially neonatal/premature infants to convert unconjugated bilirubin to more execrable compounds. Such phototherapy is integral to jaundice treatments, hyperbilirubinemia, in the case of, for example, incomplete liver development, and certain diseases and conditions. See, for example, US. 2009/0030490 A1 to Pipe, published on Jan. 29, 2009; US 2003/0029071 A1 to Whitehurst published on Mar. 7, 2003; U.S. Pat. No. 6,464,715 B1 to Gysens, published on Oct. 15, 2002; U.S. Pat. No. 4,907,132 to Parker, assigned to Luminex, published on Mar. 6, 1990; US 2007/0208397 A1 to Gardner, published on Sep. 6, 2007; US 2010/0106228 A1 to Gardner, published on Apr. 29, 2010; US 2006/0100675 A1 to Gardner, published on May 11, 2006; U.S. Pat. No. 7,246,392 B2 to Schmid, assigned to Halo Innovations, Inc., and published on Jun. 24, 2007; and U.S. Pat. No. 6,596,016 B1 to Vreman, assigned to The Board of Trustees of the Leland Stanford Junior University, published on Jul. 22, 2003, the aforementioned disclosures incorporated herein by reference in their entireties.

Such phototherapy devices typically provide light in the range of, for example, 400 nanometres (nm) to 550 nm, or 450 nm to 460 nm which helps to photoisomerise unconjugated bilirubin to, for example, lumirubin which may then be safely excreted.

Traditionally the phototherapy device may come in two basic forms. The first form is a transparent light box within which an infant is placed so as to absorb light on their skin. Such light boxes are typically quite heavy and large as they need to encompass the entire infant. Furthermore, these light boxes typically contain florescent lights which can generate significant heat, due to the intensity of light needed and the distance between the light source and the patient's skin. Infants and their tender skin are especially susceptible to irritation, dehydration, and even burning due to heat. Also, infants and especially newborns, preemies and neonatal infants are often unable to properly regulate their body temperature and thus at the other extreme, if the light box temperature is not well-controlled, the infant may suffer from hypothermia. Such light boxes are typically not mobile and the parent or caregiver is unable to hold or comfort the infant during the process which leads to stress and anxiety for the infant. In such a device, when activated, the light is often visible through the transparent walls of the light box. In such an embodiment, the infant is required to wear eye protection during this time so as to prevent eye damage due to the intense light. However, such eye protection may be dislodged as the infant moves and/or turns during the treatment. Accordingly, it is desirable to provide an improved device, treatment, or kit which is lighter, more mobile, generates less wasted heat, and which does not require eye protection which may be easily dislodged.

The second form is a device containing a light source, a light tube containing a fibre optic cable, and at least one emission portion optically-connected to the light source via the fibre optic cable. The emission portion, oftentimes a sheet or a paddle, then distributes the light to the patient's skin. Multiple emission portions are also known. The patient will either lie on the sheet/paddle in which case eye protection is again required, or may be wrapped up in a swaddle which placed the paddle or sheet in direct or almost direct contact with the patient's skin. The swaddle may be custom-made for this purpose or improvised with, for example, a blanket or towel.

In cases where the swaddle wraps the sheet/paddle against the infant's skin, then the swaddle is typically thick and opaque to the light, so as to avoid the need for the infant to wear eye protection. Yet in such a case, it may be difficult to tell if the device is activated. If the device's control panel is unreadable, then the caregiver or parent may need to take extra steps, such as turning the device, unwrapping the swaddle, etc. to tell if the phototherapy device is operational. Designing the phototherapy device with a control panel which is more easily readable may entail additional cost, and/or complexity. Accordingly, it is desirable to provide a phototherapy device which avoids the need for eye protection for the infant, which allows the parent/caregiver to comfort the infant, and for which the parent/caregiver may instantly know the status (of the device).

In situations where the light source is contained within a small housing, the light source may often be, for example, a Light Emitting Diode (LED) (see US 2009/0030490 A1, above) or a plurality thereof (see, US 2001/0106228 A1, above). In the case where a single LED is provided, the LED must be of a high enough power so as to provide the required light intensity to the patient. However, such a powerful LED tends to generate a large amount of heat as it is used over a long period of time. As such phototherapy sessions may last up to, for example 7 days, overheating and heat damage to the device must be considered, which may lead to the requirement of higher tolerance materials which may be heavier, more expensive, etc. all of which are undesirable in especially a mobile device. Accordingly, it is desirable to be better able to control the excess heat, reduce side light leakage, etc. in a phototherapy device without significantly increasing the cost, weight, etc.

SUMMARY OF THE INVENTION

An embodiment of the present invention relates to a phototherapy device containing a housing, an emission portion, and a light tube. The housing contains a light source that emits light at a wavelength of from about 400 nm to about 550 nm; or from about 425 nm to about 525 nm; or from about 440 nm to about 475 nm; or from about 450 nm to about 460 nm, and a power source is operatively-connected to the light source. The power source is located within the housing, external to the housing, or a combination thereof. The emission portion is distal from the light source and the light tube is connected between the light source and the emission portion. The light tube contains a light source end, an emission end distal from the light source end, an optical fibre within the light tube, and a mesh enclosing the optical fibre. The mesh contains an inner surface facing the optical fibre and an outer surface facing the outside environment. The mesh allows a limited amount of light to leak from the optical fibre to the outside environment, where the limited amount of light is less than about 2 $\mu W/cm^2/nm$. When the light source end is connected to the housing proximal to the light source and the emission end is connected to the emission portion, the optical fibre transmits light the length of the light tube from the light source to the emission portion.

An embodiment of the present invention also relates to a phototherapy device containing a housing, an emission portion, and a light tube. The housing contains a light source that emits light at a wavelength of from about 400 nm to about 550 nm; or from about 425 nm to about 525 nm; or from about 440 nm to about 475 nm; or from about 450 nm to about 460 nm. A light shield is located proximal to the light source, and a power source is operatively connected to the light source. The power source is located within the housing, is external to the housing, or a combination thereof. The emission portion is distal from the light source and the light tube is connected between the light source and the emission portion. The light tube contains a light source end, an emission end distal from the light source end, and an optical fibre within the light tube. When the light source end is connected to the housing proximal to the light source and the emission end is connected to the emission portion, the optical fibre transmits light the length of the light tube from the light source to the emission portion. The light shield is located between the light source and the light tube, and during operation of the phototherapy device, the light shield reduces light exposure from the light source to a part of the phototherapy device other than the light source end.

An embodiment of the present invention relates to a phototherapy kit for treating a patient containing a phototherapy device as described herein, and a swaddle.

An embodiment of the present invention relates to a method for treating a patient in need for phototherapy having the steps of providing a phototherapy device as described herein, activating the light source, exposing the patient to light from the light source for a period of time, or a predetermined period of time.

Without intending to be limited by theory, it is believed that the present invention provides an improved phototherapy device, kit and/or method which may, for example, provide one or more of the following benefits: improved efficiency, an improved user experience, a reduced waste heat, reduced heat damage to, for example, the housing and parts thereof, reduced light leakage, reduced weight, reduce expense, reduced need for eye protection, easier comforting of the patient, easier checking of the status of the phototherapy device during use, increased design flexibility, increased housing material flexibility, etc.

Figure 1:
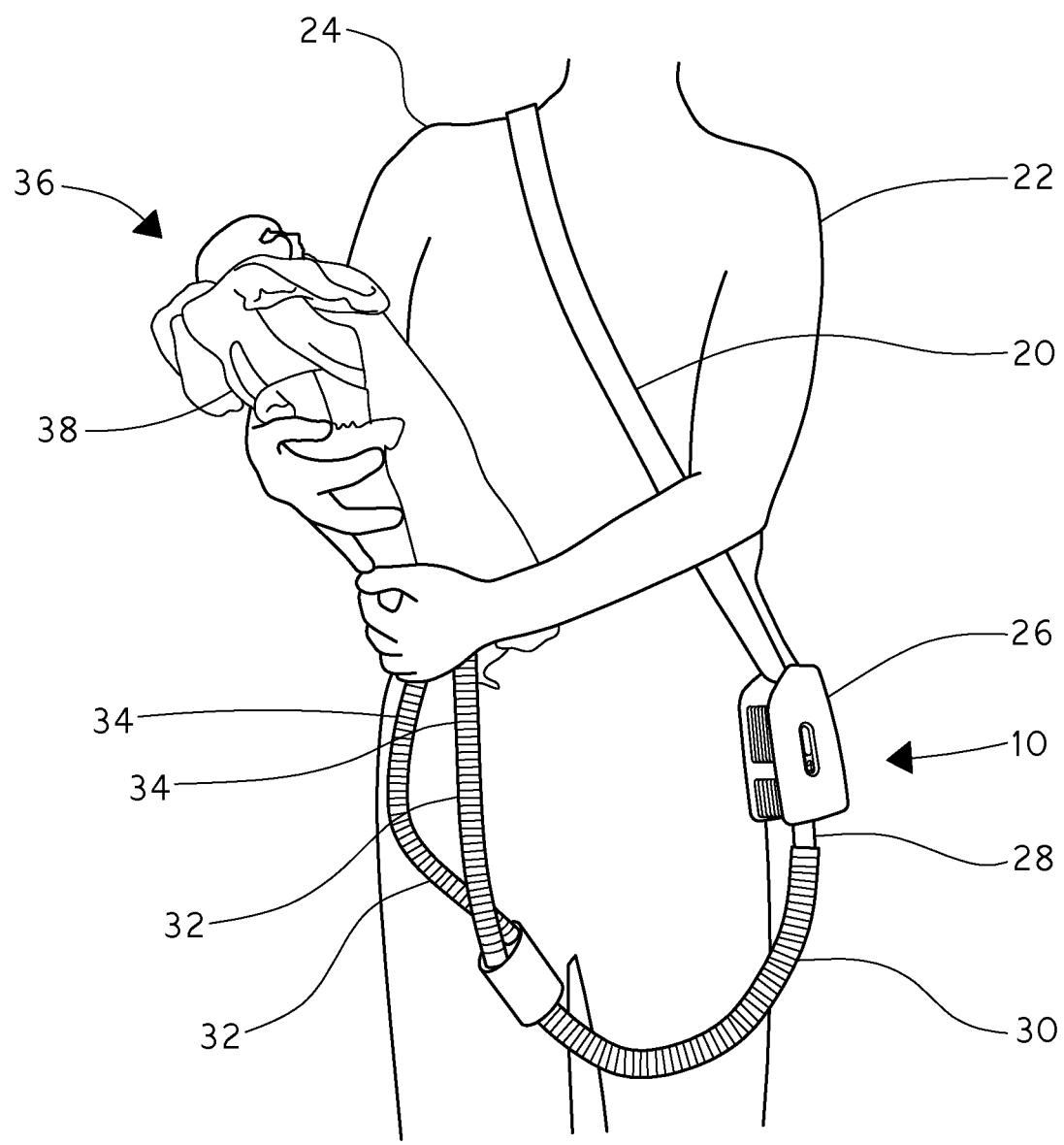
FIG. 1 shows an embodiment of the phototherapy device herein during use.

The figures herein are for illustrative purposes only and are not necessarily drawn to scale.

DETAILED DESCRIPTION OF THE EMBODIMENTS

Unless otherwise specifically provided, all tests herein are conducted at standard conditions which include a room and testing temperature of 25° C., sea level (1 atm.) pressure, pH 7, and all measurements are made in metric units. Furthermore, all percentages, ratios, etc. herein are by weight, unless specifically indicated otherwise.

In an embodiment of the present invention, a phototherapy device contains a housing, an emission portion, and a light tube. The housing contains a light source which emits light at a wavelength of form about 400 nm to about 550 nm; or from about 425 nm to about 525 nm; or from about 440 nm to about 475 nm; or from about 450 nm to about 460 nm. A power source located within the housing, external to the housing, or a combination thereof, and is operatively connected to and powers the light source. The emission portion is distal to the light source. The light tube is connected between the light source and the emission portion and contains a light source end, an emission end distal from the light source end, and an optical fibre within the light tube. A mesh encloses the optical fibre. The mesh contains an inner surface facing the optical fibre and an outer surface facing the outside environment; in other words, the outer surface is opposite from the optical fibre. When the light source end is connected to the housing proximal to the light source, and the emission end is connected to the emission portion, then the optical fibre transmits light the length of the light tube from the light source to the emission portion. The mesh allows a limited amount of light to pass from the optical fibre to the outside environment. The limited amount of light is less than about 2 $\mu W/cm^2/nm$.

In an embodiment of the present invention, a phototherapy device contains a housing, an emission portion, and a light tube. The housing contains a light source, a light shield proximal to the light source, and a power source. The housing contains a light source which emits light at a wavelength of from about 400 nm to about 550 nm; or from about 425 nm to about 525 nm; or from about 440 nm to about 475 nm; or from about 450 nm to about 460 nm. The power source located within the housing, external to the housing, or a combination thereof, and is operatively connected to and powers the light source. The emission portion is distal to the light source. The light tube contains a light source end, an emission end distal from the light source end, and an optical fibre within the light tube. The light source end is connected to the housing proximal to the light source and the emission end is connected to the emission portion. The optical fibre transmits light the length of the light tube from the light source to the emission portion. The light shield is typically located between the light source and the light tube, and during operation of the phototherapy device, the light shield reduces light exposure from the light source to a part of the phototherapy device other than the light source end; or the light shield reduces light exposure from the light source to a part of the housing; or the light shield reduces light exposure from the light source to a part of the housing other than the light tube.

The phototherapy device herein provides light treatment for a patient, especially infants, neonatal infants, and premature infants ("preemies"), as described above. The housing may be formed of any substance known in the art for making housings, typically a plastic, a polymer, a resin, a metal, rubber, a ceramic, and/or a combination thereof; or plastic, a polymer, a metal, rubber, a ceramic, and a combination thereof; or polycarbonate, polyethylene terephthalate, acrylonitrile butyl styrene, a metal, a ceramic, and a combination thereof. The housing may be moulded, or otherwise formed from these materials be methods known in the art, and may be formed of a single piece, in a clamshell, as various pieces that are later then assembled, etc. In an embodiment herein, one or more external surfaces of the housing is concave, such that if the external surface is placed down on a flat surface, any louvers (see FIG. 2 at 68) or vents are not blocked by the flat surface.

In an embodiment herein, the housing is water-resistant; or water-proof, so as to reduce the chance of any liquids contacting the inside of the housing, causing short circuits, etc. The housing may be designed so as to contain, for example, a water-resistant seal; or a water-proof seal such as, for example, a louver, a gasket, a sealant, and a combination thereof; or an o-ring; or a silicone ring; or a silicone string; or a sealant. In an embodiment herein, the housing contains a water-resistant seal; or water-proof seal, at, for example, where the housing pieces are connected, the upper casing, the lower casing, the front casing, the back casing, at or around the button(s), display, male and/or female connector(s), handle, control element, battery, and/or at any electrical connections, such as an electrical plug, a battery leads, battery compartment, etc.

In the case where the housing contains louvers, in addition to reducing the chance of light from passing through, the louvers may be designed with a tortuous path which reduces the chance of liquids from entering the housing and disrupting the electronics, power source, etc.

The light source useful herein may be any light source known in the phototherapy art, or a LED, a fluorescent light, a halogen light, a metal halide light, and a combination thereof; or a LED, a fluorescent light, a halogen light, and a combination thereof; or a LED, a halogen light, and a combination thereof. The light source useful herein typically emits light at a wavelength of from about 400 nm to about 550 nm; or from about 425 nm to about 525 nm; or from about 440 nm to about 475 nm; or from about 450 nm to about 460 nm which is believed to efficiently convert bilirubin to, for example, lumirubin. In an embodiment herein, the light source has a peak light emission from about 425 nm to about 490 nm; or from about 430 nm to about 475 nm; or from about 440 to about 470 nm.

In an embodiment herein, a light shield is contained within the housing proximal to the light source and serves to protect the phototherapy device from damage caused by heat, light, etc. The light shield is typically located between the light source and the light tube, and during operation of the phototherapy device, the light shield reduces light exposure from the light source to a part of the phototherapy device other than the light source end; or the light shield reduces light exposure from the light source to a part of the housing; or the light shield reduces light exposure from the light source to a part of the housing other than the light tube. For example, the light shield may fit over the light source and contain a hole and/or transparent aperture therein through which the light shines onto the light source end of the light tube. The light shield may therefore reduce heat damage, light damage, allow greater design and/or material flexibility, etc. The light shield reduces the amount of light and heat which reaches the housing surrounding the light source end. In addition, the light shield may be reflective or refractive thereby helping to concentrate the light onto the light source end. In an embodiment herein, the portion of the housing supporting the light source may also be reflective so as to increase the efficiency and/or intensity of the light source. In an embodiment herein, the light shield contains a metal; a ceramic, and a combination thereof; or is formed with a metal. In an embodiment herein, the light shield contains at least 1 side which is reflective to light at the wavelengths above; or the light shield contains 2 sides which are reflective to light at the wavelengths above. The light shield may operate in conjunction with, for example, a heat sink, a fan, and/or other components to help to reduce the amount of heat undesirably transmitted to other parts of the housing and/or the phototherapy device.

Without intending to be limited by theory, it is believed that such a light shield and/or reflective housing portion may reduce potential heat damage to the phototherapy device and/or provide additional flexibility to the designer to employ less expensive, and/or heavy housing materials. It is believed that such a light shield may also reduce the energy needs of the light source to provide the required light intensity to the patient.

The power source is operatively connected to and thereby provides electrical power to the light source thereby allowing it to emit light and may be located within the housing, external to the housing, or a combination thereof. The power source useful herein may be, for example, selected from the group of AC power source, DC power source, a power generator and a combination thereof; a battery, an AC power cord to connect to an AC power source/AC power grid, and a combination thereof; or a fuel cell; or a battery; or a rechargeable battery; or a rechargeable power supply; or an AC power source. For example, if the power source is a DC power source such as a battery, then it may be contained within the housing. If the power source is an AC power cord, then it may be externally connected to the housing. If the power source is a power generator, then in an embodiment herein, the power generator is a fuel cell.

In an embodiment herein, the battery, rechargeable battery, and/or rechargeable power source contains sufficient energy to power the phototherapy device (including any electronics, a fan, etc. in addition to the light source) for a period of greater than or equal to about 30 minutes; or from about 30 minutes to about 12 hours; or from about 45 minutes to about 10 hours or from about 1 hour to about 8 hours. In an embodiment the battery herein is a rechargeable battery and/or a rechargeable power source, and may be removable from the housing, or permanently installed within the housing. In an embodiment herein, the phototherapy device contains both a battery and an AC power cord. In an embodiment herein, the AC power cord may directly or indirectly transfer energy to the battery so as to recharge it.

The emission portion useful herein may be, for example, in the form of a sheet, a net, a paddle, and a combination thereof; or a paddle. Paddles are known, for example, in U.S. Pat. No. 4,907,132 at FIGS. 1-2, and may be formed of, for example, a pattern of optical fibres. The optical fibre, or more often, plurality of optical fibres, are arranged in a pattern which may then provide an even distribution of light to the patient.

The light tube useful herein contains at least two ends, specifically a light source end, and an emission end distal to the light source end. An optical fibre is contained within the light tube. The light source end is connected to the housing at a location proximal to the light source so that the light source shines into the light source end. The light is then carried along the optical fibre to the emission end where it is connected, or optically connected, to the emission portion. The optical fibre then emits the light at the emission portion so that it can illuminate and/or be absorbed by the patient's skin.

The optical fibre useful herein transmits light from the light source to the patient, typically the patient's skin. The optical fibre useful herein should therefore be capable of efficiently transporting light in the wavelengths of from about 400 nm to about 550 nm; or from about 425 nm to about 525 nm; or from about 440 nm to about 475 nm; or from about 450 nm to about 460 nm. The optical fibres useful herein may be selected from a side-glow optical fibre, an end-glow optical fibre and a combination thereof; or an end-glow optical fibre. Such optical fibres are available from a variety of vendors worldwide.

Without intending to be limited by theory, it is believed that the end-glow optical fibre provides more efficient transmission of the light. Specifically, an end-glow optical fibre is believed to typically possess reduced light dissipation along its length as compared to a side-glow optical fibre. This property also reduces the need for shielding along the light tube, so as to achieve the same light output at the emission portion. In addition, the use of end-glow optical fibres reduces attenuation, increases light transmission efficiency, etc. and thus allows the use of a lower power light source, which in turn leads to additional benefits such as reduced heat dissipation requirements, reduced power usage, a reduced/smaller heat sink, a smaller housing, a lighter device, a smaller fan further requiring less energy, lower battery/power source weight, etc.

In an embodiment herein, the optical fibre includes a plurality of optical fibres; or from about 2 optical fibres to about 10000 optical fibres; or from about 10 optical fibres to about 7500 optical fibres; or from about 500 optical fibres to about 4500 optical fibres. In an embodiment herein, the plurality of optical fibres is provided as a bundle of (individual) optical fibres, as known in the art and as described, for example, in U.S. Pat. No. 4,907,132 (noted above). In an embodiment herein, the diameter of each individual optical fibre is of a substantially uniform diameter and ranges from about 0.05 millimetres (mm) to about 1 mm; or from about 0.1 mm to about 0.75 mm; or from about 0.15 to about 0.5 mm.

In an embodiment herein, the optical fibres are arranged in a layer at the emission portion; or a plurality of layers at the emission portion.

In an embodiment herein the optical fibre bundle is randomized and cut into a pattern on the emission portion so as to generate an evenly-dispersed light pattern on the patient. In an embodiment herein, the light tube contains an optical fibre bundle containing a plurality of end-glow optical fibres.

While end-glow optical fibres may be used it is recognized that such fibres still allow some leakage of light from the sides of the fibres. Accordingly, in an embodiment of the present invention the light tube, the optical fibre, the optical fibre bundle, or combination thereof is enclosed within a mesh. If a plurality of light tubes are present, then in an embodiment herein, each light tube is enclosed within a mesh. The mesh useful herein contains an inner surface which faces the optical fibre and an outer surface facing the outside environment; in other words, the outer surface is opposite from the optical fibre. The outer surface does not need to actually touch the outside environment, as it may be enclosed within the light tube, wrapped in a transparent to translucent plastic, etc. As noted herein, when the light source end is connected to the housing proximal to the light source, and the emission end is connected to the emission portion, then the optical fibre transmits light the length of the light tube from the light source to the emission portion. The mesh allows a limited amount of light to leak from the optical fibre (through the light tube) to the outside environment. The limited amount of light is less than or equal to about 2 $\mu W/cm^2/nm$, or from about 0 $\mu W/cm^2/nm$ to about 2 $\mu W/cm^2/nm$; or from about 0.0001 $\mu W/cm^2/nm$ to about 2 $\mu W/cm^2/nm$; or from about 1 $\mu W/cm^2/nm$; or from about 0.0005 $\mu W/cm^2/nm$ to about 1.5 $\mu W/cm^2/nm$; or from about 0.001 $\mu W/cm^2/nm$ to about 1 $\mu W/cm^2/nm$. In an embodiment herein the mesh is made from woven fibres, a non-woven material, a sheet, and a combination thereof; or woven fibres, a non-woven material, and a combination thereof; or woven fibres. In an embodiment herein, the mesh is formed from nylon, plastic, and a combination thereof; or nylon.

In an embodiment herein, the mesh is formed of a translucent material which allows less than about 20%; or from about 0.001% to about 20%; or from about 0.01% to about 15%; or from about 0.1% to about 10%, of the light at a wavelength of 455 nm to pass through it. The phrase "formed of a translucent material" indicates that the material itself is opticallytranslucent, and therefore the material per se allows light to pass through it.

In an embodiment herein, the mesh is formed of an opaque material, and comprises a plurality of holes; or a plurality of holes having an average hole size of from about 0.01 $mm^2$ to about 10 $mm^2$; or from about 0.05 $mm^2$ to about 5 $mm^2$; or from about 0.1 $mm^2$ to about 4 $mm^2$. The phrase "formed of an opaque material" indicates that the material itself is optically-opaque at the relevant wavelength, and therefore the material per se does not allow light to pass through it, but instead that any light passing through the mesh must pass through, for example, the holes therein.

In an embodiment herein, the mesh allows less than about 20%; or from about 0.001% to about 20%; or from about 0.01% to about 15%; or from about 0.1% to about 10%, of the light at a wavelength of 455 nm to pass through it. Such light may, for example, pass directly through the mesh via the holes, and/or through the mesh's material per se.

Meshes useful herein having the above properties are available from multiple suppliers around the world.

Without intending to be limited by theory, it is believed that the leakage of such a level of light is below the level which could be harmful to the normal person's eyes, and therefore is safe. Furthermore, the parent/caregiver can easily see the glow of the light leaking from the mesh in the light tube and therefore the parent/caregiver does not need to look at the housing to see whether or not the phototherapy device is working, powered on, etc. Especially if the housing is being suspended from the body while the infant/patient is being carried in a swaddle, the light can be a convenient indicator of when the phototherapy device is active, so that the parent/caregiver does not need to turn their neck in an uncomfortable position, etc.

In an embodiment herein, the phototherapy device contains a plurality of light tubes, or from about 2 light tubes to about 10 light tubes; or from about 2 to about 6 light tubes; or from about 2 light tubes to about 4 light tubes; or about 2 light tubes. Typically each light tube will contain an optical fibre; or a bundle of optical fibres, therein which then lead to an emission portion, and therefore in an embodiment herein the number of light tubes is equal to the number of emission portions. Without intending to be limited by theory, it is believed that a plurality of light tubes and the corresponding emission portions may be desirable to, for example, illuminate different parts of the patient. For example, a first emission portion may illuminate the ventral side of the patient, a second emission portion may illuminate the dorsal side of the patient, a third emission portion may illuminate the right side of the patent, a fourth emission portion may illuminate the left side of the patient, etc. In an embodiment herein, a single light tube may be connected, or removably-connected to the housing, and may then branch out into a plurality of secondary light tubes; or from about 2 secondary light tubes to about 10 secondary light tubes; or from about 2 secondary to about 6 secondary light tubes; or from about 2 secondary light tubes to about 4 secondary light tubes; or about 2 secondary light tubes, which are then each connected to an emission portion. In such an embodiment, the light tube would contain all of the optical fibres which then branch off to the secondary light tubes.

In an embodiment herein, the phototherapy device contains a freely-rotatable connection system between the housing and the light tube. When connected, such a rotatable connection allows the light tube to rotate around the long axis without disconnecting from the housing. Without intending to be limited by theory, this is believed to be especially helpful when the infant is moving and/or needs to be held and positions in different alignments and directions. As the light tube may freely rotate about the long axis, the light tube is unlikely to become tangled or twisted during use.

In an embodiment herein, the freely-rotatable connection system contains a channel-ball connection system. As used herein, a channel-ball connection system contains one or more balls such as a ball-bearing which is subjected to radial pressure by a spring. Typically the housing contains a female connector while the light source end of the light tube contains a complementary male connector. The female connector contains one or more balls located in a radially-oriented ring in the interior of the housing. The balls are biased towards the centre of the radius with a mechanical, electrical, and/or magnetic biasing element, such as a spring, an elastic retainer, a permanent magnet and/or an electromagnet, and a combination thereof; or a spring, an elastic ring, a resilient plastic or metal structure, and a combination thereof. A male connector has a terminal end portion and a narrow portion a bit distal from the end. In an embodiment herein the narrow portion is a radial channel such as a ring-like furrow. The male connector is inserted into the female connector where the terminal end portion applies outward radial pressure against the ball(s). The terminal end portion pushes the ball(s) against the biasing element(s) and allows the terminal end portion to move past the ball(s). Once the more-narrow portion is reached, then the ball(s) snaps back into place due to the pressure from the biasing element(s) and the pressure on the ball(s) holds the male connector in place with the biased ball(s) pressed into the radial channel. However, since the balls are free to rotate, the male connector may rotate along the long axis without becoming unconnected from the female connector.

When the male connector is to be released, the process is reversed, where the male connector is pulled out of the female connector and the wider portion pushes the ball(s) against the biasing element(s) until the wider portion is past the ball(s). Then the male connector disengages form the female connector.

In an embodiment herein, the phototherapy device contains a control element. The control element may contain, for example, a power switch, a microprocessor, a timer, a wireless communication device, a global position system locator, a memory storage, an emergency alarm, a sensor, and a combination thereof; or a power switch, a microprocessor, a timer, a wireless communication device, a global position system locator, a memory storage, an emergency alarm, a temperature sensor, and a combination thereof. These elements may be physically located together with the control element, or may be operatively-connected thereto (for example, via wires or a wireless communication device) from locations such as, for example, the swaddle, the housing, etc.

The power switch may be, for example, a plurality of power switches such as, a simple mechanical power switch, or a complicated electrical power switch. The microprocessor useful herein may control one or more aspects of the phototherapy device, such as, for example, activating and deactivating the light source, power management/usage, the intensity of the light source, the fan, and a combination thereof. The control element may also contain, for example, a timer, a wireless communication device, a global position system locator, a memory storage, an emergency alarm, a temperature sensor, and a combination thereof. The control element is typically operatively connected to, for example, the light source, the power source, and a combination thereof.

In an embodiment herein, the control element contains a timer. The timer may be set to, for example, activate the light source at a predetermined time, or after a predetermined period of time. Alternatively, the timer may deactivate the light source after a predetermined period of time. In an embodiment herein, the predetermined period of time is from about greater than or equal to about 30 minutes; or from about 30 minutes to about 12 hours; or from about 45 minutes to about 10 hours or from about 1 hour to about 8 hours. The timer is therefore typically operatively connected to the light source as well as the power source. In an embodiment herein, the timer also operatively-connects with a memory storage, the light source, and the power source to record the time; or total amount of time, that the patient has used the phototherapy device when the light source is turned on.

The emergency alarm may be programmed to sound if, for example, there is an unexpected event, such as overheating, a loss of power, etc.

The sensor useful herein may be, for example, a temperature sensor (e.g., to detect overheating), a motion sensor, a light sensor, a location sensor, a current sensor, a moisture sensor, a microspectrometer sensor, and a combination thereof.

In an embodiment herein, the current sensor may be provided so as to detect, for example, a short circuit, if the light source burns out or otherwise becomes inoperable, etc. In an embodiment herein, the moisture sensor is present to detect, for example, sweat, urine, etc. and may be present in the swaddle. In an embodiment herein, the microspectrometer sensor (see FIG. 6 at is present to detect, the bilirubin present in the patient/infant's skin, and may be present/integrated into the inside surface (see FIG. 6 at 110) of the swaddle (see FIG. 1 at 38).

The sensor herein may be operatively connected to the control element by, for example, a wire; or a plurality of wires; or a wireless communication device.

In an embodiment herein, the invention; or the phototherapy device; or the phototherapy kit; or the control element; or the swaddle; or the emission cover; or the emission portion; or a combination thereof, contains a wireless communication device; or a plurality of wireless communication devices. Such a wireless communication device may be useful to, for example, transfer data to and/or from a central data storage unit, to send or receive alerts and/or messages, to send or receive instructions, to receive software updates, and a combination thereof. The wireless communication device may employ, for example, a wireless communication standard such as a radio frequency (RF) communication standard, an infrared (IR) communications standard, a near field communication (NFC), a microwave communication standard, and a combination thereof. In an embodiment herein, the RF communication standard is selected from the group of a cellular (2G, 3G, 4G, 5G, LTE, CDMA, etc.) standard, Bluetooth™, Wi-Fi™, Z-Wave™, ZigBee™, and a combination thereof; or Bluetooth™; or a Wi-Fi™

Phototherapy Kit

An embodiment of the present invention includes a phototherapy kit for treating a patient. The phototherapy kit may contain a phototherapy device and a swaddle. The swaddle useful herein typically contains a cloth base layer which is designed to snugly wrap around the patient's, typically an infant's, body. The swaddle typically further may contain an emission portion position, or a plurality of positions, for the emission portion. For example, the emission portion may be placed on the swaddle and the infant then placed on the emission portion such that when the swaddle is closed and wrapped around the patient, the emission portion is directly, or almost directly touching the patient's skin. Such a swaddle is especially useful if the emission portion is, for example, a sheet or a paddle. In an embodiment herein, the swaddle contains a number or emission portion positions equal to the number of emission portions.

The swaddle may further contain one or more fasteners to close the swaddle and keep it snugly wrapped around the patient. Such fasteners may include, for example, hook and loop fasteners (i.e., Velcro™), buttons, magnets, zippers, screws, clips, adhesive fasteners, snaps, ties, elastic bands, and a combination thereof; or hook and loop fasteners, ties, and a combination thereof.

In an embodiment herein, the phototherapy kit further contains a harness. The harness is used to carry an item, for example, the housing, the swaddle, the power source, the patient/infant, and a combination thereof; or the housing, the power source, and a combination thereof. The harness is typically removably-attachable to the item. The harness may attach to any of the above items via an attachment such as a clip.

In an embodiment herein, the phototherapy kit further contains an emission cover which is used to hold the emission portion in place in the swaddle, to prevent skin, oils, liquids, and/or dirt from contaminating the emission portion, and/or to otherwise prevent the patient's skin from directly-contacting the emission portion. Such an emission cover may be, for example, a sleeve or pouch into which the emission portion slides and/or fits. The emission cover may be attached; or removably-attached, to the inside of the swaddle such that the emission cover directly contacts the skin of the patient when the swaddle is snugly wrapped around the patient. The emission portion should be sufficiently transparent to the light from the emission portion, such that it does not significantly inhibit the transmission of light to the patient. Thus, an emission cover formed of, for example, a webbing, lace, a nonwoven material, an optically-transparent plastic, an substantially optically transparent material at the relevant light wavelengths, and a combination thereof may be useful herein. Such an emission cover may be formed of a fabric made of, for example, cotton, nylon, silk, plastic, and a combination thereof; or cotton, a nonwoven fabric, a plastic, and a combination thereof.

In an embodiment herein, the emission cover is removably-attached to the swaddle by a fastener. In an embodiment herein, the emission cover is located at least partially between the patient's skin and the emission portion. In an embodiment herein, at least 90% of the light from the emission portion passes through the emission cover; or from about 90% to about 100% of the light from the emission portion passes through the emission cover; or from about 95% to about 100% of the light from the emission portion passes through the emission cover; or from about 97% to about 100% of the light from the emission portion passes through the emission cover; or form about 98% to about 100% of the light from the emission portion passes through the emission cover.

In an embodiment herein, the phototherapy kit contains a stand for connecting to the housing. The stand may, for example, hold the phototherapy device during use and/or for storage.

Phototherapy Method:

An embodiment of the invention herein includes a method for treating a patient in need for phototherapy. The treatment includes the steps of providing a phototherapy device, for example, as described herein, activating the light source, exposing the patient to light from the light source for a period of time; or a predetermined period of time.

In an embodiment herein, the patient is an infant; or a neonatal infant; or a preemie. In an embodiment herein, the patient is an infant with hyperbilirubinemia.

Turning to the Figures, FIG. 1 shows a side view of an embodiment of a phototherapy device, 10, in use and removably-attached to a harness, 20. The harness, 20, is convenient worn by the parent/caregiver, 22, and suspended across the shoulder, 24. The phototherapy device, 10, has a housing, 26, which is attached; or removably-attached, to the light source end, 28, of a light tube, 30. The light tube, 30, branches into 2 secondary light tubes, 32, closer to the emission end, 34, which are distal from the light source end, 28.

Figure 3:
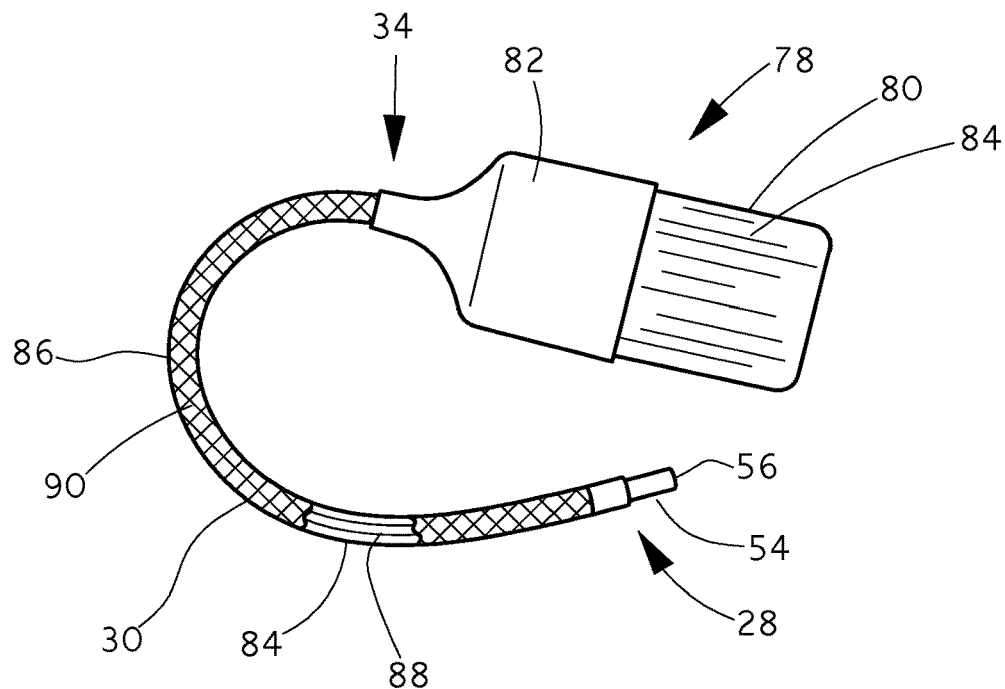
FIG. 3 shows a partially cut-away top view of an embodiment of an emission portion and a light tube useful herein.

The patient/infant, 36, is wrapped in a swaddle, 38, which also enwraps the emission portions (see FIG. 3 at 78). Without intending to be limited by theory, it is believed that such a phototherapy device and method of use are convenient, allow parent/caregiver—patient/infant interaction and soothing and improved medical outcomes.

Figure 2:
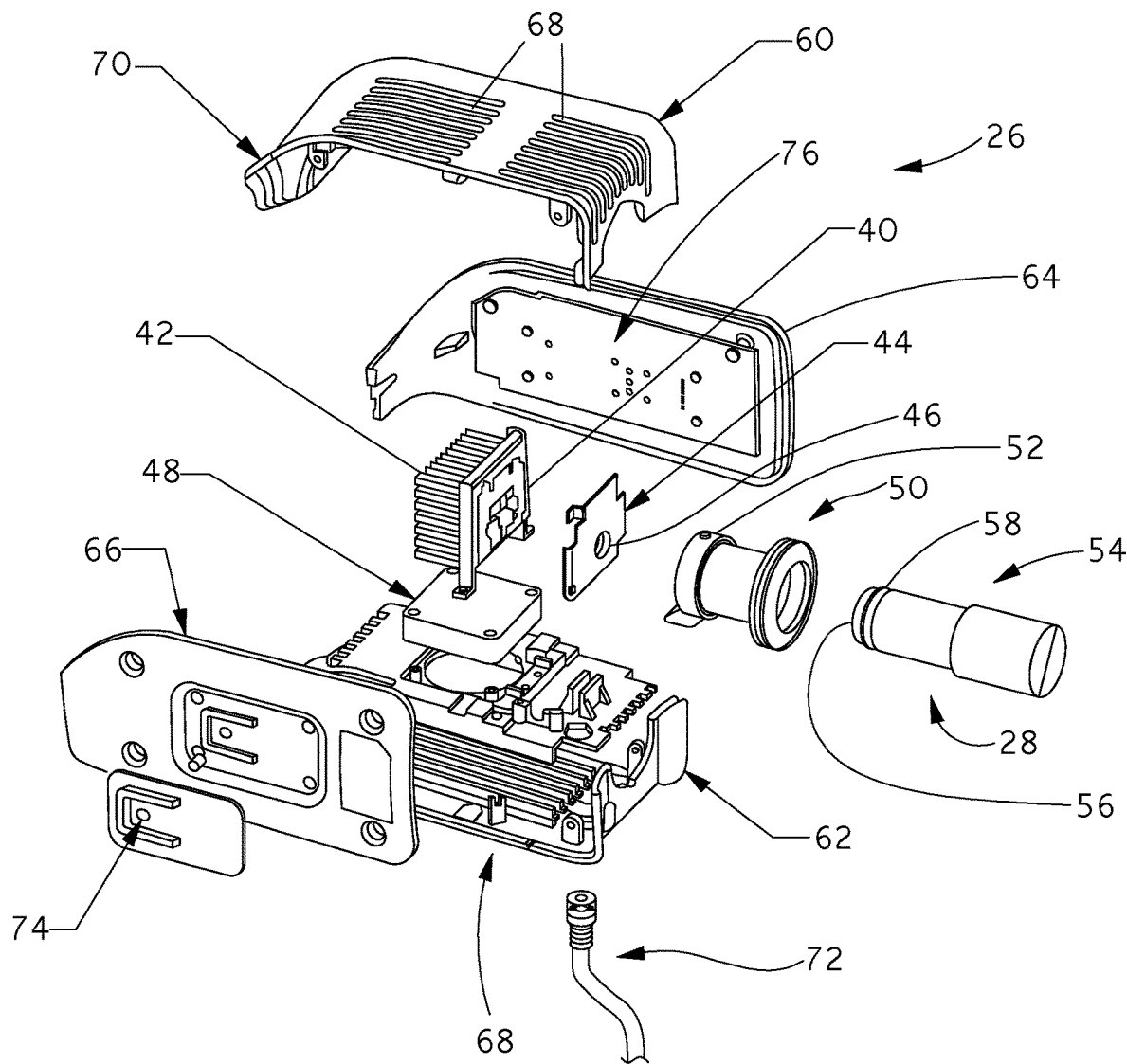
FIG. 2 shows an exploded view of an embodiment of the housing useful herein.

FIG. 2 shows an exploded view of an embodiment of a housing, 26, containing a light source, 40, which in this case is a LED emitting light in the range of about 450 nm to about 460 nm. The light source is physically-connected to a heat sink, 42, which helps to draw away and dissipate heat from the light source, 40. Opposite the heat sink, 42, from the light source, 40, is a light shield, 44, which covers the light source, 40. As the light source, 40, may be omni-directional, the light shield, 44, is placed so as to reduce the potential heat damage to the rest of the housing, 26. The light shield, 44, contains an aperture, 46, through which the light from the light source, 40, passes. A fan, 48, is mounted directly adjacent to the heat sink and blows air transversely across the heat sink, 42, the light source, 40, and the light shield, 44.

The housing, 26, further contains a female connector, 50, which is proximal to the light source, 40, and is embedded in the housing, 26. The female connector, 50, contains a channel-ball connection system, 52, which corresponds with the male connector, 54, having a terminal end portion, 56, at the light source end, 28. The terminal portion is adjacent to a narrow portion, 58, which in FIG. 2 is a radial channel.

The housing, 26, also contains an upper casing, 60, which fits together with an opposing lower casing, 62. The housing also contains a front casing, 64, and a back casing, 66 opposite the front casing, 64. The upper casing, 60, and the lower casing, 62, both contain a concave surface and a plurality of opposing louvers, 68, which allow air to/from the fan, 48, to pass through to cool the interior of the housing, 26. In this embodiment, the louvers, 68, allow air to pass though, but the gaps therebetween do not form a straight path, thus preventing light from the light source, 40, from leaking directly out of the housing, 38. This in turn reduces the chance of inadvertent eye damage to the user and/or the patient. The upper casing, 60, also contains a handle, 70, for carrying the housing, 26. The lower casing, 62, further contains a power source, 72, which in FIG. 2 is an external AC power cord.

The back casing, 66, further contains an attachment, 74, which in FIG. 2 is a clip which mates with, for example, a harness (see FIG. 1 at 20) to allow the housing to be supported and/or carried thereupon.

The housing, 26, further contains a control element, 76, which is a contains a microprocessor containing, for example, a timer, a wireless communication device, a GPS locator, a memory storage, a sensor, etc. The control element, 76, is operatively connected to the light source, 40, and the power source, 72.

FIG. 3 shows a partially-cut-away top view of a light tube, 30, and an emission portion, 78, which contains a paddle, 80, and a transition piece, 82. The paddle, 80, contains a plurality of optical fibres, 84, which carry light from the light source end, 28, to the emission portion, 78, where it is released to illuminate the patient. The transition portion, 82, aligns and fixes the location of the plurality of optical fibres, 84, on the paddle, 80, so that they do not move relative to the rest of the emission portion, 78. A mesh, 86, encloses a plurality of optical fibres, 84, within the light tube, 30 from the light source end, 28, to the emission end, 34. The mesh has a inner surface, 88, which is facing the optical fibre, 84, and an outer surface, 90, which is facing the outside environment, and is distal from the optical fibre. However, as mentioned herein, the mesh may allow a limited amount of light to pass from the optical fibre, 84, to the outside environment; in other words, the outer surface, 90, is on the opposite side of the mesh from the optical fibre, 84.

Figure 4:
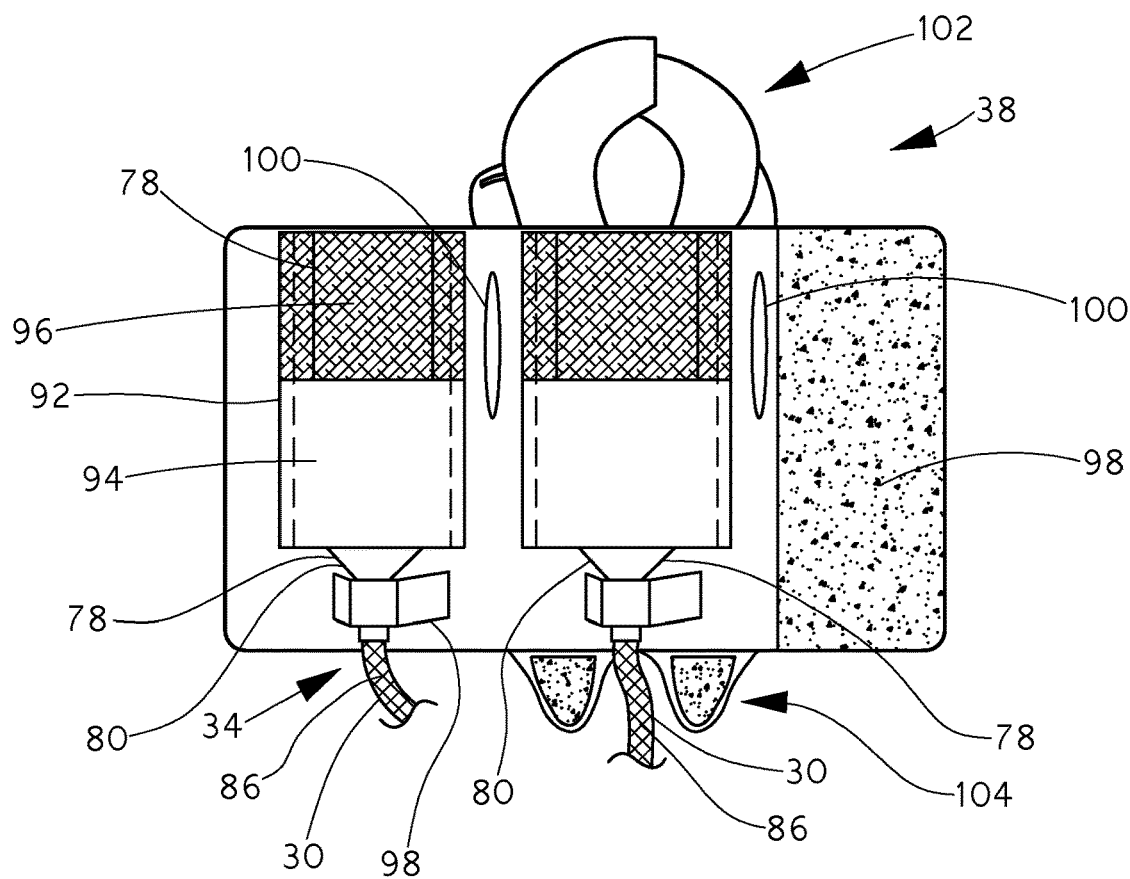
FIG. 4 shows a plan open view of an embodiment of a swaddle useful herein.

FIG. 4 shows a top view of an embodiment of a swaddle, 38, containing two emission portions, 78, which in this case are in the form of paddles, 80, attached to light tubes, 30. The optical fibres (see FIG. 3 at 84) are enclosed by a mesh. 86. The swaddle, 38, further contains an emission cover, 92, covering each paddle, 80, to hold the paddle, 80, in place and also to prevent the paddle, 80, from becoming soiled. The emission covers, 92, may be either permanently affixed to the swaddle, 38, or may be removable, as desired. The emission cover, 92, contains an opaque area, 94, and a substantially optically transparent; or optically-transparent, area, 96, which is formed of a webbing, such as cheesecloth. Therefore, the light emitted from the emission portion, 78, may illuminate the patient's skin.

The swaddle, 38, further contains a plurality of fasteners, 98, which may, for example, secure the swaddle, 38, closed and ensure a snug fit for the patient, hold the emission portion, 78, in place at the emission end, 34, etc.

In FIG. 4, the swaddle further contains a pair of arm holes, 100 for the patient's arms to fit through, as well as a head area, 102, containing a hat, and booties, 104 for the patient's feet located opposite the head area.

Figure 5:
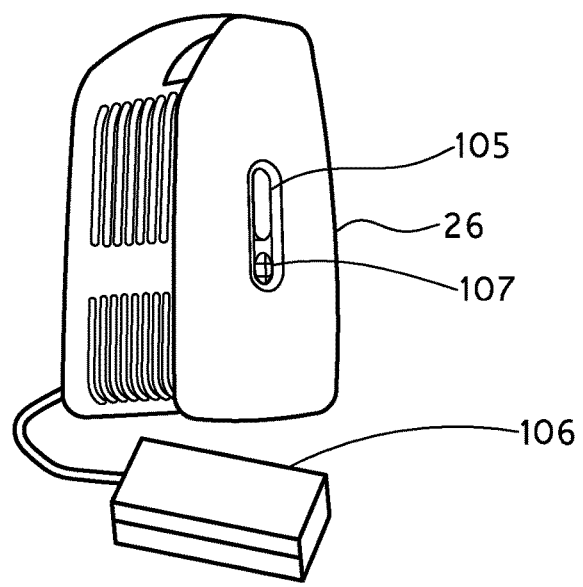
FIG. 5 shows a side view of an embodiment of the housing useful herein.

FIG. 5 shows a side perspective view of a housing, 26, having a display, 105, for providing information to the user/caregiver, a battery, 106, and a power button, 107, attached thereto. In this embodiment, the battery, 106, is an external battery pack, but an internal battery is also useful herein.

Figure 6:
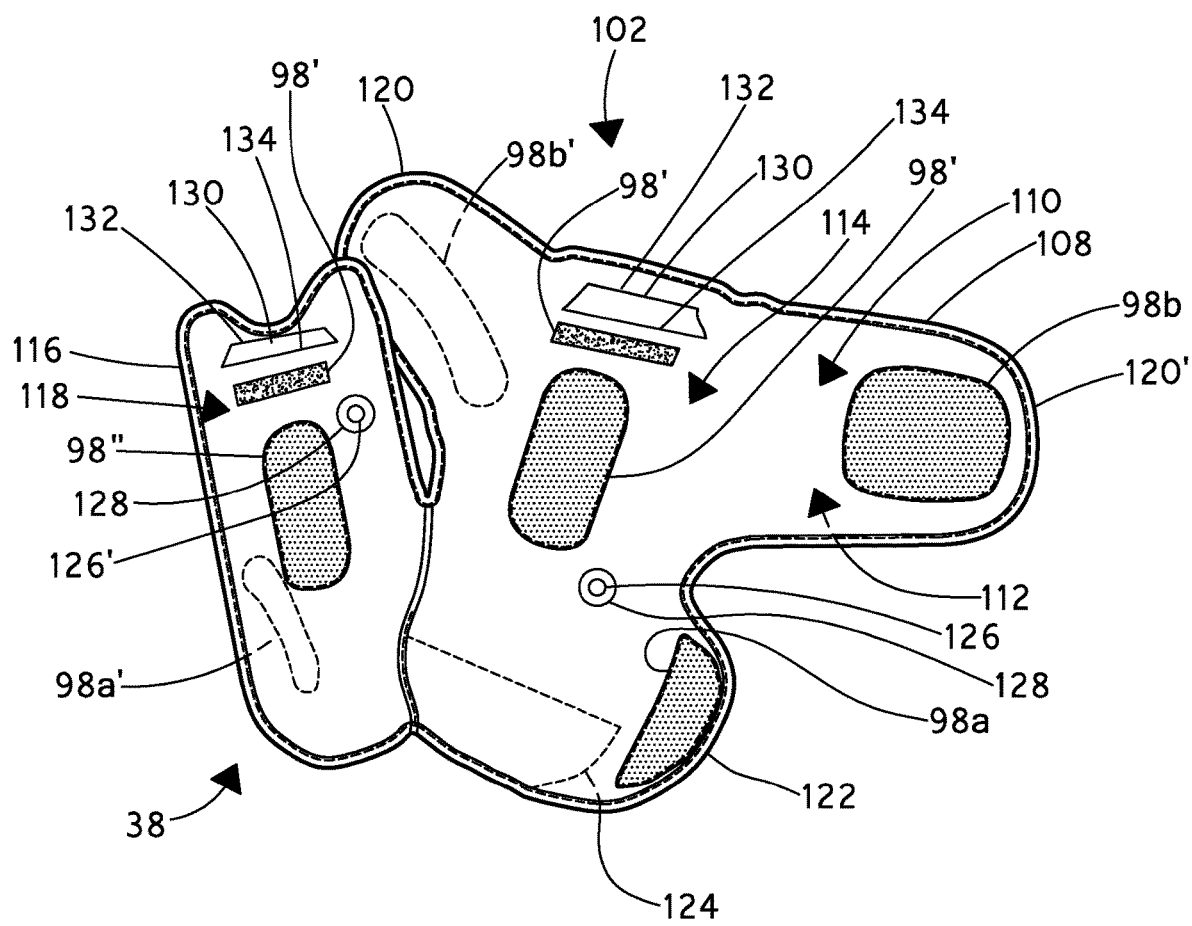
FIG. 6 shows a plan open view of an embodiment of a swaddle useful herein.

FIG. 6 shows a top plan view of the inside of an embodiment of a swaddle, 38, useful herein. The swaddle, 38, is formed or machine-washable fabric such as cotton which is substantially opaque to the light from the emission portions (see FIG. 3 at 78). Without intending to be limited by theory, it is believed that it is highly preferred to have the swaddle made of an easily washable material, especially since it would typically be used with an infant who is mostly or completely naked so as to maximise the skin illuminated by the light. The swaddle, 38, is surrounded by a sewn hem, 108, which prevents material fraying during washing and cleaning.

The swaddle, 38, contains a plurality of fasteners, 98*a*, 98*a*', 98*b*, 98*b*', which are corresponding hook and loop fasteners on the inside surface, 110 (98 *a*, 98*b*), and the outside surface, 112 (98*a*', 98*b*'), which help to close the swaddle and thereby keep the patient warm and feeling secure. In addition to fasteners present to hold the swaddle, 38, closed, a plurality of fasteners 98' are present to hold the emission cover (see FIG. 4 at 92) and/or the emission portion (see FIG. 3 at 78) securely onto the swaddle, 38, during use. In FIG. 6, the fasteners, 98', may be, for example, the loop-side of a hook-and-loop fastener system, the hook-side of a hook-and-loop fastener system; or the hook-side of a hook-and-loop fastener system. The emission cover (see FIG. 4 at 98) may then possess the corresponding side of the hook-and-loop fastener system.

In an embodiment herein, the swaddle, 38, contains a fastener, 98'; or a plurality of fasteners, for holding the emission cover (see FIG. 4 at 92); or a plurality of fasteners for each emission cover, where the fastener is the hook-side of a hook-and-loop fastener system. Furthermore, in an embodiment herein, the side of the emission cover (see FIG. 4 at 98) facing the fastener, 98' (i.e., the hook-side) on the swaddle, 38, is formed of a lace, a nonwoven fabric material, and a combination thereof. Without intending to be limited by theory, it is believed that if the appropriate portion of the emission cover is formed of lace, a nonwoven fabric material, etc. then this may adhere to the hook-side fasteners without the need for a special loop-side to be attached to or formed in the emission cover. In an alternate embodiment herein, the hook side of a hook-and-loop fastener is provided on the emission cover (see FIG. 4 at 98) and the loop side of a hook-and-loop fastener is provided on the swaddle, 38. It is believed that such a design may reduce potential scratching from the hooks of the patient/infant, in case the infant is placed on (or wrapped in) the swaddle without a emission cover in place, or if the emission cover is forgotten by the user/caregiver.

To use the swaddle in FIG. 6, the parent/caregiver would insert the emission portions (see FIG. 4 at 78) into the appropriate emission covers (see FIG. 4 at 92). A first emission cover (see FIG. 4 at 92 containing the emission portion (see FIG. 4 at 78)) is placed on the dorsal side, 114, of the swaddle, 38, and aligned with the fastener, 98'. The second emission cover (see FIG. 4 at 92, containing the emission portion (see FIG. 4 at 78)) is aligned with the fastener, 98', located on the ventral flap, 116, of the ventral side, 118, of the swaddle, 38. The patient is then placed on the swaddle, 38, lying on its back and resting on the dorsal side, 114, with the emission cover (see FIG. 4 at 92) adjacent with the patient's skin and aligned such that the emission portion (see FIG. 4 at 78) can illuminate the patient's skin. The ventral flap, 116, is then closed over the patient, with the emission cover (see FIG. 4 at 92) adjacent with the patient's skin and aligned such that the emission portion (see FIG. 4 at 78) can illuminate the patient's skin.

The swaddle contains a pair of opposing upper flaps, 120 and 120', as well. The upper flap, 120, may then be folded over the ventral flap, 116, and the opposing upper flap, 120', may be also folded over the ventral flap, 116, such that fastener, 98*b*, attaches to fastener 98*b*' to secure the swaddle, 38, closed. Similarly, the lower flap, 122, may then be folded over the ventral flap, 116, so that the fastener, 98*a*, attaches to fastener, 98*a*', on the ventral flap, 116. The combination of the ventral flap, 116, and the attached fastener pairs, 98*a*-98*a*' and 98*b*-98*b*', assure that the patient is securely and comfortably secured in the closed swaddle, 38.

In the embodiment in FIG. 6, a pocket, 124, is formed on the outside surface, 112, of the swaddle, 38. The pocket may be reversed so as to securely and snugly hold the patient's feet to increase their comfort and reduce body heat loss.

In the embodiment of FIG. 6, a sensor, 126, is located on inside surface, 110, of the swaddle, 38, which detects moisture such as sweat, urine, etc. The sensor is operatively connected to a wireless communication device, 128, to communicate with the control element (see FIG. 2 at 76). In FIG. 6, a microspectrometer sensor, 126', is also present on inside surface, 110, of the swaddle, 38. The microspectrometer sensor, 126', detects the transcutaneous bilirubin level in the infant/patient's skin and communicates this with the control element via a wireless communication device, 128. Without having to be limited by theory, it is believed that such a sensor placed on the inside surface of the swaddle provides significant benefits, as the patient/infant's bilirubin levels may be measured without having to stop treatment, take off the swaddle, etc.

In the embodiment of FIG. 6, the swaddle, 38, further contains a stopper element, 130, which is a flap of fabric which is attached to the swaddle, 38, at the attachment side, 132, and is unattached at the free side, 134. The edge of the emission portion (see FIG. 3 at 78) slides under the free side, 134, and is stopped by the connected attachment side, 132. Without intending to be limited by theory, it is believed that the stopper reduces slippage or movement of the emission portion (see FIG. 3 at 78) when the patient/infant squirms or moves.

It should be understood that the above only illustrates and describes examples whereby the present invention may be carried out, and that modifications and/or alterations may be made thereto without departing from the spirit of the invention.

It should also be understood that certain features of the invention, which are, for clarity, described in the context of separate embodiments, may also be provided in combination in a single embodiment. Conversely, various features of the invention which are, for brevity, described in the context of a single embodiment, may also be provided separately, or in any suitable subcombination.

All references specifically cited herein are hereby incorporated by reference in their entireties. However, the citation or incorporation of such a reference is not necessarily an admission as to its appropriateness, citability, and/or availability as prior art to/against the present invention.

What is claimed is:

1. A phototherapy device comprising:
   A) a housing comprising:
      i) a light source wherein the light source emits light at a wavelength in a range selected from the group consisting of from about 400 nm to about 550 nm, from about 425 nm to about 525 nm, from about 440 nm to about 475 nm, and from about 450 nm to about 460 nm;
      ii) a light shield proximal to the light source; and
      iii) a power source operatively-connected to the light source, wherein the power source is located within the housing, external to the housing, or a combination thereof;
   B) an emission portion distal from the light source; and
   C) a light tube comprising:
      i) a light source end;
      ii) an emission end distal from the light source end;
      iii) an optical fibre within the light tube; and
      iv) a mesh enclosing the optical fibre, the mesh comprising:
         a) an inner surface facing the optical fibre; and
         b) an outer surface facing an outside environment,
      wherein the mesh allows a limited amount of light to leak from the optical fibre to the outside environment, and wherein the limited amount of light is from about 0.0001 $\mu W/cm^2/nm$ to about 2 $\mu W/cm^2/nm$,
      wherein the light source end is connected to the housing proximal to the light source and the emission end is connected to the emission portion, wherein the optical fibre transmits light the length of the light tube from the light source to the emission portion,
   wherein the light shield is located between the light source and the light tube, and wherein the light shield reduces light exposure from the light source to a part of the phototherapy device other than the light source end.

2. The phototherapy device according to claim 1, wherein the light shield comprises a metal, a ceramic, or a combination thereof.

3. The phototherapy device according to claim 1, wherein the optical fibre is an end-glow optical fibre.

4. The phototherapy device according to claim 1, further comprising a freely-rotatable connection system; or a channel-ball connection system, connecting the housing and the light tube.

5. A phototherapy kit for treating a patient, the phototherapy kit comprising:
   A) a phototherapy device according to claim 1; and
   B) a swaddle for containing the emission portion.

6. The phototherapy kit according to claim 5, further comprising a harness attachable removably to the housing, the swaddle, or a combination thereof.

7. The phototherapy kit according to claim 5, further comprising:
   C) an emission cover, wherein the emission cover attaches to the swaddle, and wherein the emission cover is located at least partially between a patient's skin and the emission portion.

8. A method for treating a patient in need of phototherapy, comprising the steps of:
   A) providing a phototherapy device according to claim 1;
   B) activating the light source; and
   C) exposing a patient to a light emitted from the emission portion for a period of time.

9. The method according to claim 8, wherein the patient is an infant.

10. The phototherapy device according to claim 1, wherein the housing further comprises:
    v) a heat sink connected to the light source; and
    vi) a fan adjacent to the heat sink, wherein the fan blows air transversely across the heat sink.

11. A mobile phototherapy device comprising:
    A) a housing comprising:
       i) a light source wherein the light source emits light at a wavelength in a range selected from the group consisting of from about 400 nm to about 550 nm, from about 425 nm to about 525 nm, from about 440 nm to about 475 nm, and from about 450 nm to about 460 nm;

ii) a housing connector for connecting a light tube;

iii) a light shield proximal to the light source and located between the light source and the housing connector, configured to reduce light exposure from the light source to a part of the housing other than the light tube; and iv) a power source operatively-connected to the light source, wherein the power source is located within the housing, external to the housing, or a combination thereof;

B) a light tube connected between the light source and the emission portion, the light tube comprising:

i) a light source end connected to the housing connector of the housing;

ii) an emission end distal from the light source end;

iii) an optical fibre within the light tube configured for transmitting light the length of the light tube, from the light source end to the emission end; and iv) a mesh enclosing the optical fibre, the mesh comprising:

a) an inner surface facing the optical fibre; and b) an outer surface facing an outside environment, wherein the mesh allows a limited amount of light to leak from the optical fibre to the outside environment, and wherein the limited amount of light is from about 0.0001 µW/cm$^2$/nm to about 2 µW/cm$^2$/nm; and C) an emission portion connected to the emission end of the light tube, to release light transmitted through the optical fibre to a patient.

12. The phototherapy device according to claim 11, wherein the light shield comprises a metal, a ceramic, or a combination thereof.

13. The phototherapy device according to claim 11, wherein the optical fibre is an end-glow optical fibre.

14. The phototherapy device according to claim 11, further comprising a freely-rotatable connection system; or a channel-ball connection system, connecting the housing and the light tube.

15. A phototherapy kit for treating a patient, the phototherapy kit comprising:

A) a phototherapy device according to claim 11; and

B) a swaddle for containing the emission portion.

16. The phototherapy kit according to claim 15, further comprising a harness attachable removably to the housing, the swaddle, or a combination thereof.

17. The phototherapy kit according to claim 15, further comprising:

C) an emission cover, wherein the emission cover attaches to the swaddle, and wherein the emission cover is located at least partially between a patient's skin and the emission portion.

18. A method for treating a patient in need of phototherapy, comprising the steps of:

A) providing a phototherapy device according to claim 11;

B) activating the light source; and

C) exposing a patient to a light emitted from the emission portion for a period of time.

19. The method according to claim 18, wherein the patient is an infant.

20. The phototherapy device according to claim 11, wherein the housing further comprises:

v) a heat sink connected to the light source; and vi) a fan adjacent to the heat sink, wherein the fan blows air transversely across the heat sink.

* * * * *